United States Patent [19]

Singleton

[11] Patent Number: 4,638,084

[45] Date of Patent: Jan. 20, 1987

[54] PROCESS FOR DIMERIZING ACRYLATES AND METHACRYLATES

[75] Inventor: David M. Singleton, Houston, Tex.

[73] Assignee: Shell Oil Company, Houston, Tex.

[21] Appl. No.: 775,077

[22] Filed: Sep. 12, 1985

[51] Int. Cl.$^4$ ............................................. C07C 67/343
[52] U.S. Cl. ................................... 560/202; 502/102; 562/590; 562/592
[58] Field of Search .......................... 560/202; 502/102

[56] References Cited

U.S. PATENT DOCUMENTS 3,013,066  12/1961  Alderson .............................. 560/202
3,560,561  2/1971   Scheben et al. ................. 560/202 X
4,451,665  5/1984   Nugent ................................ 560/202

OTHER PUBLICATIONS

Oehne & Pracejus, Tetrahedron Letters, No. 4, pp. 343–348, 1979.
Alderson et al, J. Am. Chem. Soc., 87, pp. 5638–5645, 1965.

*Primary Examiner*—Natalie Trousof
*Assistant Examiner*—Vera C. Clarke

[57] ABSTRACT

A process is disclosed for dimerizing lower alkyl acrylates or lower alkyl methacrylates utilizing a bis(ethylene) rhodium tetrafluoroborate catalyst.

7 Claims, No Drawings

PROCESS FOR DIMERIZING ACRYLATES AND METHACRYLATES

FIELD OF THE INVENTION

This invention relates to a process for dimerizing esters of acrylic acid and methacrylic acid to esters of, respectively, hexenedioic acid and dimethylhexenedioic acid.

BACKGROUND OF THE INVENTION

There are several references in the literature to the use of palladium compounds for the dimerization of acrylate esters. For example, U.S. Pat. No. 4,451,665, issued May 29, 1984, disclosed the use of tetrakis(hydrocarbylnitrile)palladium(II)tetrafluoroborate as a catalyst for the dimerization of acrylate and methacrylate esters. Oehne and Pracejus, in Tetrahydron Letters (1979, pp 343-348) discloses the use of a dimerization catalyst prepared from bis(benzonitrile)palladium(II)dichloride and silver tetrafluoroborate. Alderson et al, Journal of the American Chemical Society (1965) 87 pp 5638-5645 discloses the use of rhodium chloride in an uncomplexed form to dimerize methyl acrylate.

Dialkyl hexenedioates are readily convertible to adipic acid (hexanedioic acid) by hydrogenation and subsequence hydrolysis. Adipic acid in turn is used in large volume in the production of the condensation polymers, particularly Nylon 66. Therefore, even a small improvement in any method for making dialkyl hexenedioates can be of major commercial significance.

A system that will catalyze the dimerization of methacrylate esters to "linear" diesters, that is, 2,5-dimethylhexenedioates, which are the products having the longest possible chain with terminal alkoxycarbonyl groups, is also a desirable objective. 2,5-Dimethylhexanedioic acid, available from dialkyl 2,5-dimethylhexenedioates, is also useful in making condensation polymers such as polyamids and polyesters.

SUMMARY OF THE INVENTION

The instant invention relates to a process for dimerizing a lower alkyl acrylate or a lower alkyl methacrylate to the corresponding dialkyl hexenedioates and dialkyl 2,5-dimethylhexenedioates by contact with a catalyst prepared by reacting chloroobis(ethylene)rhodium(I)dimer and silver tetrafluoroborate. The instant catalyst provides an alternative to known palladium catalysts and provides a dimerization process with high selectivity to "linear" that is, unbranched, dimers at low dimerization temperatures with high conversions and yields.

DESCRIPTION OF THE PREFERRED EMBODIMENTS

The invention resides in the process which comprises contacting a lower alkyl acrylate or lower alkyl methacrylate, with lower alkyl being alkyl of 1 to 8 carbon atoms with a catalyst prepared by reacting chlorobis(ethylene)rhodium(I)dimer with silver tetrafluoroborate, optionally in the presence of a free radical inhibitor for acrylate or methacrylate polymerization inhibition, which process is carried out at a temperature between about 0° C. to about 150° C., more preferably between about 20° C. and about 75° C., to produce one or more dialkyl hexenedioates (from the alkyl acrylate) or a dialkyl 2,5-dimethylhexenedioates (from the alkyl methacrylate).

The size of the alkyl group in the alkyl acrylate or alkyl methacrylate is not critical. However, lower alkyl, of one to eight carbon atoms, acrylates and methacrylates are preferred because of their availability, and the methyl and ethyl esters are especially preferred because of the ease of isolation of the resultant reaction products. Particularly preferred are the methyl acrylates and methyl methacrylates. The alkyl group can be substituted with any group that does not interfere with the desired reaction.

The catalyst used in the instant dimerization process is typically prepared by reacting chlorobis(ethylene)rhodium(I)dimer, $((C_2H_2)_2RhCl)_2$, and silver tetrafluoroborate, $AgBF_4$, in the presence of an olefin to retard decomposition to the metal. The catalyst may be prepared in situ in the presence of the methacrylate or acrylate to be dimerized, or more preferably the catalyst may be prepared utilizing another olefin, and the total reaction mixture is then used then to catalyze the dimerization reaction. One advantage of the instant catalyst is that it is particularly suited for the selective dimerization of acrylates and methacrylates even in the presence of other olefins. Thus, the use of an olefins such as, hexene or octene in the catalyst preparation technique does not effect the subsequent dimerization of the acrylate or the methacrylate to give a pure hexenedioate product. Both the chlorobis(ethylene)rhodium-(I)dimer and the silver tetrafluoroborate are readily available commercially. Typically, about one mole of tetrafluoroborate is used with half a mole of the dimer although differing amounts, particularly, greater amounts can be utilized.

The amount of rhodium catalyst charged depends largely on the amount of alkyl acrylate or methacrylate used, and the ratio of moles of alkyl acrylate or alkyl methacrylate to gram atoms of rhodium can vary widely. Usually, to permit efficient use of the catalyst, the ratio is at least about 10:1 and can be as high as about 10000:1, more preferably between about 20:1 to about 1000:1. It is also desirable in the reaction mixture to add a sufficient amount of a free radical inhibitor to prevent polymerization of the acrylates and methacrylates. These inhibitors are well known in the art and include for example, hydroquinone, 2,4,6-tri(tertiarybutyl)-phenol, 2,6-di(isobutyl)-4-tertiary butyl phenol, and the like. Typically, amounts of inhibitor utilized comprise less than about 1 mole percent of the initial acrylate or methacrylate charge.

The instant process can be conducted over a rather broad range of temperature, for example, from about 0° C. to about 150° C., although 100° C. is a preferred maximum. The temperature chosen will depend on such variables as the particular acrylate or methacrylate to be dimerized, the catalyst concentration, and the time over which it is convenient or desired to operate the process. For example, when methacrylate is dimerized a convenient temperature of operation ranges from about 35° C. to about 75° C. The times of reaction can very widely, from a few minutes to several days. Preferably, the reaction is carried out in about 15 minutes to about 72 hours.

The process of the instant invention is illustrated by the following example which is provided for illustration only and is not to be construed as limiting the invention.

EXAMPLE I

The following example describes the preparation of the catalyst and its use in the dimerization of methyl acrylate.

To an 80 ml autoclave were added 36.4 ml of 1-octene, 1.90 g (5 mmole) of chlorobis(ethylene)rhodium(I)dimer obtained from steam Chemicals, 1.9 g (10 mmole) of silver tetrafluoroborate and 5 ml of cyclohexane to be used as a marker in subsequent product analysis. The reactor was sealed and stirred at ambient temperature in order to allow the catalyst reaction to take place. Then, 15 ml of methacrylate containing 0.02%w hydroquinone were added to the autoclave. The autoclave was heated to about 48° C. for about 1.3 hours and then cooled and a sample removed. The autoclave was reheated to 68° F. for about 1.3 hours, then cooled, sampled, and reheated to 78° C. for about 14.5 hours. Results for these experiments are shown in the table following. The quantitative data for the dimethyl hexenedioate was obtained by assuming the same GC factor as was established for methyl acrylate. The identity of the dimethyl hexenedioate was confirmed by GC/MS and NMR.

COMPARATIVE EXAMPLE A

In this example, only bischloro(ethylene)rhodium(I)-dimer was utilized as the catalyst and no silver tetrafluoroborate was used. In this case the reaction temperature had to be raised to over 100° C. in order to obtain significant conversions. Results are shown in the table. Without the use of the silver tetrafluoroborate, significant quantities of the "linear" hexenedioate are not obtained.

| Catalyst | Deg C | Hrs | % Conv[a] | % Yield[b] | Turnovers (hr$^{-1}$) MeAcr.[c] | Ester[d] |
|---|---|---|---|---|---|---|
| I | 48 | 1.3 | 37 | 48 | 4.7 | 2.2 |
|  | 68 | 1.3 | 73 | 64 | 4.7 | 3.7 |
|  | 78 | 14.5 | 100 | 60 | 0.3 | 0.14 |
| A | 101 | 1.0 | 4 | 41 | 0.7 | 0.3 |
|  | 143 | 0.8 | 16 | 27 | 2.5 | 0.6 |
|  | 152 | 16.0 | 33 | 21 | 0.2 | 0.03 |

[a]Percent methyl acrylate converted.
[b]Moles ester product formed per 100 moles methyl acrylate converted, where ester product = dimethylhexenedioate for I (corr. for stoichiometry)
= methylundecenoate for A.
[c]Incremental moles methyl acrylate converted/mole catalyst/hour.
[d]Incremental moles ester product formed/mole catalyst/hour.
where ester product = dimethylhexenedioate for I.
= methyl undecenoate for A.

I claim:
1. A catalytic dimerization process comprising contacting, at about 0° C. to about 150° C., a lower alkyl acrylate or lower alkyl methacrylate with lower alkyl being alkyl of 1 to 8 carbon atoms with a catalyst prepared by reacting chlorobis(ethylene)rhodium(I)dimer and silver tetrafluoroborate in a mole ratio of dimer to tetrafluoroborate of about 0.5:1 and wherein the ratio of moles of acrylate or methacrylate to gram atoms of rhodium ranges from about 10:1 to about 10000:1.
2. The process of claim 1 wherein the temperature is about 20° C. to about 75° C.
3. The process of claim 2 wherein the lower alkyl acrylate is methyl acrylate.
4. The process of claim 3 wherein the temperature is about 35° C. to about 75° C.
5. The process of claim 1 wherein there is also present a free-radical inhibitor to inhibit acrylate and methacrylate polymerization.
6. The process of claim 5 wherein the free-radical inhibitor is hydroquinone.
7. The process of claim 1 wherein the catalyst is prepared by reacting chlorobis(ethylene)rhodium(I)dimer and silver tetrafluoroborate in a mole ratio of dimer to tetrafluoroborate of about 0.5:1 in the presence of an olefin.

* * * * *